United States Patent [19]
Tomioka et al.

[11] Patent Number: 5,651,978
[45] Date of Patent: Jul. 29, 1997

[54] SILVER THIOSULFATE SILICA GEL ANTIBACTERIAL COMPOSITIONS

[75] Inventors: Toshikazu Tomioka, Ibaraki; Katsumi Tomita; Hiroaki Oka, both of Hirakata; Kenji Hoshino, Takatsuki; Atsushi Nishino, Neyagawa, all of Japan

[73] Assignee: Matsushita Electric Industrial Co., Ltd., Osaka-fu, Japan

[21] Appl. No.: 693,496

[22] Filed: Aug. 2, 1996

Related U.S. Application Data

[63] Continuation of Ser. No. 241,511, May 12, 1994, abandoned.

[30] Foreign Application Priority Data

May 18, 1993 [JP] Japan ................. 5-115725
Aug. 23, 1993 [JP] Japan ................. 5-207664
Dec. 28, 1993 [JP] Japan ................. 5-337765

[51] Int. Cl.$^6$ ......................... A01N 25/26
[52] U.S. Cl. ................. 424/421; 424/404; 424/405; 424/419; 424/420; 424/618; 424/724
[58] Field of Search .................. 424/405, 409, 424/421, 76.9, 618, 724, 404

[56] References Cited

FOREIGN PATENT DOCUMENTS

| 0488269 | 6/1992 | European Pat. Off. |
| 59-222404 | 12/1984 | Japan. |
| 59-222405 | 12/1984 | Japan. |
| 2-291900 | 12/1990 | Japan. |
| 6-39368 | 5/1994 | Japan. |

*Primary Examiner*—Neil S. Levy
*Attorney, Agent, or Firm*—Panitch Schwarze Jacobs & Nadel, P.C.

[57] ABSTRACT

An antibacterial composition having a heat-resistant property sufficient for avoiding its decomposition or discoloration at the resin molding temperature comprises; a silver thiosulfate complex salt carried on silica gel particles having an equilibrium water content of 10% or smaller, wherein at least part of the surface of the silica gel particles carrying said silver thiosulfate complex salt is covered with a coating layer composed of silicon dioxide formed by means of hydrolysis of an alkoxysilane.

4 Claims, 3 Drawing Sheets

SILVER THIOSULFATE SILICA GEL ANTIBACTERIAL COMPOSITIONS

This application is a continuation of Ser. No. 08/241,511, filed May 12, 1994, now abandoned.

BACKGROUND OF THE INVENTION

1. Field of the Invention

The present invention relates to an antibacterial composition and a method for preparing the antibacterial composition.

2. Description of the Related Art

As various synthetic resin products have been used more frequently in recent years, contamination of the surface of synthetic resin products with bacteria has become a problem when they are utilized in the fields which require the care about hygiene, such as in the field of kitchen utensils. Bacteria and fungi may grow on the surface of caulking materials utilized for interior material in the field of architecture and may cause problems in hygiene or in appearance and so on.

In order to cope with these problems, an antibacterial and antifungal composition has been mixed with a synthetic resin for the purpose of exuding the composition from the resin thereby to provide an antibacterial and antifungal properties on the surface of the resin.

Further, in order to obtain an antibacterial and antifungal effect on the surface of the resin and its surroundings by facilitating the exudation of the antibacterial and antifungal composition from the synthetic resin, an organic antibacterial and antifungal material such as thiabendazole or the like is used.

It is also known that terpene compounds among plant extracts have an antibacterial effect. For instance, there is already known a refrigerator or an air refresher (or cleaner) that is equipped with an antifungal deodorant unit comprising phytontid obtained from a plant.

It is also known an example of providing the synthetic resin products with an antibacterial effect by incorporating a certain kind of antibacterial agent of a silver salt into the resin product.

The above-mentioned organic antibacterial and antifungal agents have however disadvantages in the following points. First, because of its volatility, the surrounding environment of the synthetic resin product will be polluted when the organic antibacterial and antifungal agents are incorporated in the synthetic resin products. Further, waste water or other fluid which had been contacted with the surface of the synthetic resin products becomes to contain the antibacterial and antifungal agent. Drainage or other fluid would become a cause for a sewage pollution which in turn would seriously influence activated sludge during effluent treatment in a sewage treatment plant.

Further, many of the substances existing in the plants described above are aromatic and volatile. It is therefore impossible to incorporate these substance in the synthetic resin product, because these substances volatilize at heating when mixed with heated and melted resin for molding.

On the other hand, the silver salt antibacterial agents have a disadvantage that silver ion of the agents would be allowed to react with chloride ion in tap water to form insoluble silver chloride, resulting in a loss of its antibacterial effect. Further, the silver salts which have a high photochemical reactivity suffer another disadvantage that they become black and deteriorate their antibacterial performance by being converted into metal silver or silver oxide. In addition, the silver salt antibacterial agents have a further disadvantage that in case of incorporating them in the resin by kneading or compounding and the resin is molded at a heating temperature of 200° C. or above, it is difficult to obtain a white or transparent resin molded product because the antibacterial agents may sometimes discolor or make a dull color at the heating temperature during the molding process.

SUMMARY OF THE INVENTION

It is a primary object of the present invention to provide an antibacterial composition that obviates the above-mentioned disadvantages and deficiencies inherent to the prior art silver salt antibacterial agents and compositions. The antibacterial composition in accordance with the present invention hardly produces white turbid by the contact with the tap water, and demonstrates a stable antibacterial effect on the surface of the resin product.

It is another object of the present invention to provide an antibacterial composition that hardly becomes a cause for the environmental pollution even if it is exuded from the resin product.

It is a further object of the present invention to provide an antibacterial composition that will not be discolored at the molding temperature of the resin and can give a white or transparent resin molded product.

The present invention provides an antibacterial composition comprising a silver thiosulfate complex salt and silica gel particles, the silica gel particles having an equilibrium water content of 10% by weight or smaller at room temperature and an ordinary humidity (25° C., relative humidity: 70%), and carrying said silver thiosulfate complex salt.

Although a potassium salt and a sodium salt can be used as the silver thiosulfate complex salt, the potassium salt is preferred in point of view of its thermal stability in particular.

Silica gel particles as the carrier having two hydroxyl groups (—OH) or less for $nm^2$ of their surface are particularly preferred in point of view of the thermal stability of the carried silver thiosulfate complex salt.

In the above-mentioned antibacterial composition of the present invention, at least part of the surface of the silica gel particulate carrier is preferably covered with a coating layer.

In compliance with a covering area, thickness, porosity, and the like of the layer of the coating material, the degree and rate of releasing of the silver thiosulfate complex salt carried on the carrier are properly controlled.

Although the silver thiosulfate complex salt is difficult to obtain as a single substance in a solid state, it is possible to immobilize the salt in a state of being carried on a carrier, by first preparing as a water soluble compound, then impregnating a silica gel carrier with an aqueous solution of the compound, and drying the impregnated carrier as will be described in the followings.

The silver thiosulfate complex salt can be obtained by adding at least one salt selected from the group consisting of a sulfite salt and a hydrogen sulfite salt to a water soluble silver salt, and then adding a thiosulfate salt.

Each of said sulfite salt, hydrogen sulfite salt and thiosulfate salt is preferably a sodium salt, and more preferably a potassium salt.

The present invention further provides an antibacterial composition comprising a potassium salt of silver thiosulfate complex carried on silica gel particles.

While the novel features of the present invention are set fourth particularly in the appended claims, the invention, both as to organization and content, will be better understood and appreciated, along with other objects and features thereof, from the following detailed description taken in conjunction with the attached drawings.

DESCRIPTION OF THE PREFERRED EMBODIMENT

Figure 1:
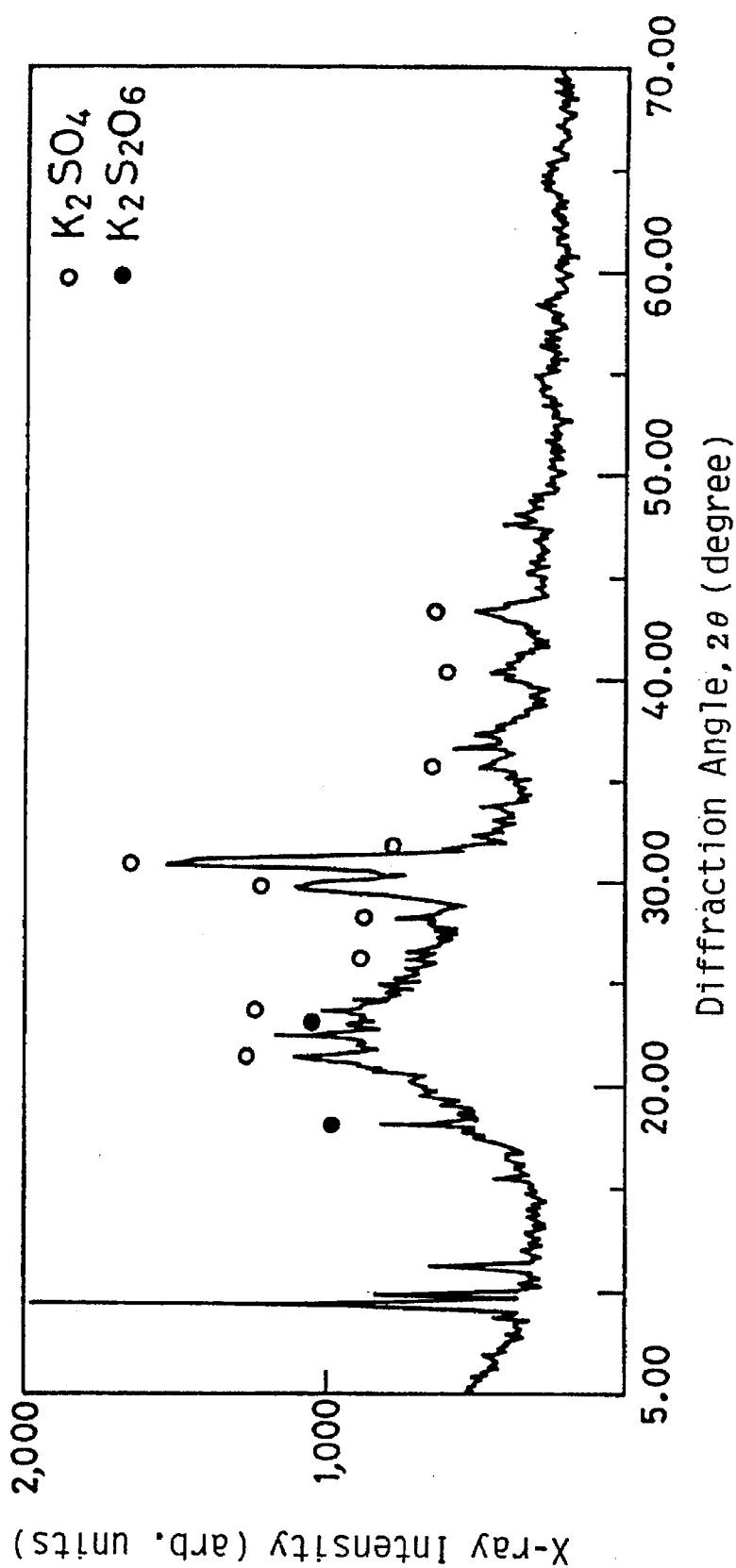
FIG. 1 is an X-ray diffraction pattern of the antibacterial composition prepared in accordance with one embodiment of the present invention.

The silver thiosulfate complex salts used in the present invention form radicals near them by an action of oxygen in the air, and the radicals exert an influence on the surface of a membrane of the microorganism which accesses to the radicals and thus the silver salts demonstrate the antibacterial activities. Such an influence is called oligodyamic reaction. That is, it is presumed that the silver thiosulfate complex salts convert the oxygen near the salts into an active oxygen by their catalytic action. The active oxygen gives a damage on a cell membrane covering the surface of the microorganism and demonstrates their antibacterial actions on the microorganisms by giving a defect on a genetic information, thereby suppressing the growth of the microorganisms.

In the following paragraphs, preferred embodiments of the present invention will be described with reference to the attached drawings.

The antibacterial composition of the present invention comprises silica gel particles which are the porous carrier, and a silver thiosulfate complex salt carried on the silica gel. Preferred silica gel is of silica gel particles having a mean particle size of 1–100 μm, and is in particular, B-type silica gel defined in the Japanese Industrial Standard (JIS) Z 0701. Among the silica gels, a silica gel which has an equilibrium water content of 10% by weight at 25° C. and a relative humidity of 70% is preferred, and, in particular, that having the surface hydroxyl (—OH) groups in a rate of 2/nm$^2$ or less is preferred. The equilibrium water content of the silica gel is determined by the water bonded to the surface —OH groups by hydrogen bonds. Therefore, the equilibrium water content depends on the number of the surface —OH groups. The silica gel having the surface —OH groups in a rate of 2/nm$^2$ or less is preferred. Such a silica gel can be obtained by heat-treating a starting material therefor at a temperature of 800°–1200° C. in the atmosphere. The period for the heat treatment can be shortened if the temperature is high. Suitable heat-treatment period is 10–0.1 hours.

The antibacterial agent of the silver thiosulfate complex salt carried on the above-defined silica gel hardly evaporates and is stable to heat, thereby to demonstrate its antibacterial effect for a long period. The above-defined silica gel is transparent and its refractive index is analogous to that of the synthetic resin. Therefore, even if the silica gel carrying the antibacterial agent is mixed with the synthetic resin by kneading, the silica gel would not change the color of the resin product.

Preparation

A preferred antibacterial composition of the present invention is prepared, for instance, in the following procedure. First, an aqueous solution of the silver thiosulfate complex salt is prepared by, for instance, adding potassium sulfite and potassium thiosulfate to an aqueous solution of silver acetate. The preparation of the aqueous solution of the silver thiosulfate complex salt is suitably performed between a temperature of about 40° C. and about room temperature. Then, a porous particulate carrier of silica gel is impregnated with the thus obtained aqueous solution and then dried, thereby to immobilize the contained silver thiosulfate complex salt in the carried state.

The drying step is suitably performed under a pressure ranging from the atmospheric pressure to $10^{-4}$ Pa at a temperature ranging from 40° C. to 120° C., in order to avoid a possible decomposition of the silver complex salt. Although it is not apparent in what state are the above-mentioned silver salts carried on the carrier, it is possible to identify the silver compounds carried on the carrier by means of X-ray diffraction pattern with a Kα ray of Cu.

FIG. 1 shows the X-ray diffraction pattern, and there is recognized diffraction lines of $K_2S_2O_6$ and $K_2SO_4$, as well as some intensity of diffraction at 8.7°, 9.4°, 9.8° and 11.2° of the diffraction angle 2θ, respectively which are not recorded in the JCPDS (Joint Committee on Powder Diffraction Standards) card.

In the above-mentioned step of causing the silver salts to be carried on the carrier, if the drying temperature is raised to about 250° C. or above, the X-ray powder diffractions peculiar to the silver compounds disappear.

FIG. 1 shows the X-ray diffraction pattern of the antibacterial composition obtained by the drying temperature at 100° C. or below.

Figure 2:
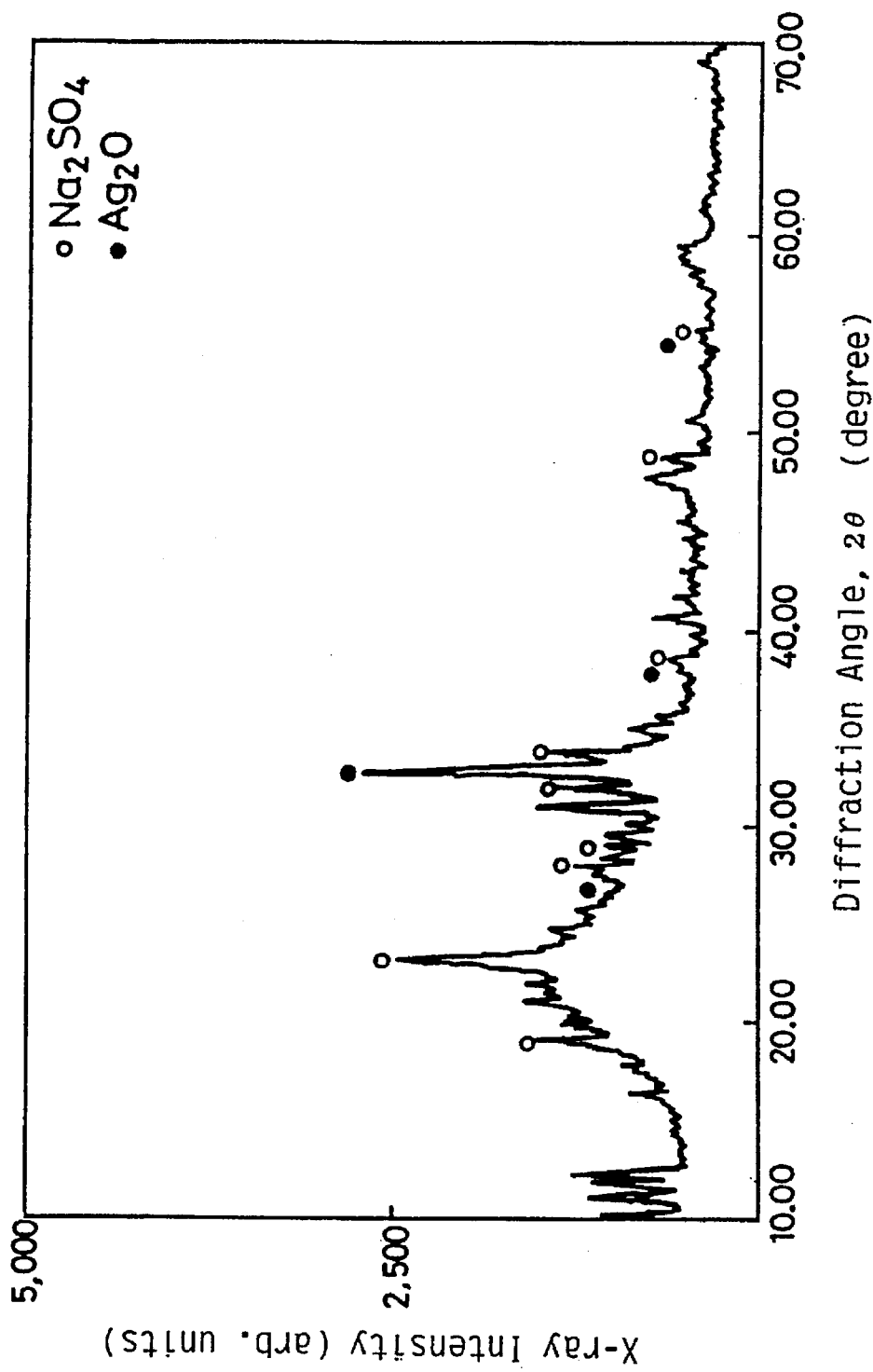
FIG. 2 is an X-ray diffraction pattern of the antibacterial composition prepared in accordance with another embodiment of the present invention.

Although all potassium salts of the sulfite and thiosulfate are employed in preparing the above-mentioned silver thiosulfate complex salt, an X-ray diffraction pattern of the antibacterial composition obtained by employing sodium salts is shown in FIG. 2. In FIG. 2, there is clearly recognized diffraction lines of $Na_2SO_4$ and $Ag_2O$, as well as some intensity of diffraction at 10.3°, 11.2°, 11.9° and 12.3° of the diffraction angle 2θ, respectively.

As above-mentioned, the silver thiosulfate complex salt for being carried on the silica gel can be prepared by adding at least one salt selected from the group consisting of sulfite salt and hydrogen sulfite salt to an aqueous solution of a water soluble silver salt, for instance, silver acetate, silver sulfate and silver nitrate. In preparing the silver thiosulfate complex salt, it is preferable to use 100–1000 parts by weight of thiosulfate salt for 100 parts by weight of the silver salt, and in a case of using sulfite salt and/or hydrogen sulfite salt, it is preferable to use 400–2000 parts by weight of the sulfite salt and/or hydrogen sulfite salt, respectively for 100 parts by weight of the silver salt.

As thiosulfate salt employed for preparing the silver thiosulfate complex salt, there are exemplified potassium thiosulfate, sodium thiosulfate, ammonium thiosulfate, and the like. As the sulfite salt, there are exemplified potassium sulfite, sodium sulfite, ammonium sulfite, potassium metasulfite and the like. As the hydrogen sulfite salt, there are exemplified potassium hydrogen sulfite, sodium hydrogen sulfite, ammonium hydrogen sulfite and the like.

Further, an antibacterial composition having an excellent thermal stability can be obtained with a molar ratio of $S_2O_3^{2-}/Ag^+$ in a range between 1 and 3 or a range between 5 and 8.

In the thus obtained aqueous solution, silver thiosulfate complex ions represented by [Ag $(S_2O_3)$]$^-$, [Ag$(S_2O_3)_2$]$^{3-}$, and the like, are existing together, in addition to thiosulfate ions and silver ions. In view of the fact that the aqueous solution does not produce any remarkable white turbid even when it is brought in contact with tap water containing chlorine, it is presumed that most of the silver ions are in a form of the complex ions.

The amount of these silver thiosulfate complex salts in a percent value converted into the amount silver to be carried on the silica gel is preferably 0.1–5 parts by weight and is more preferably 1–3 parts by weight for 100 parts by weight of the silica gel.

As the material for the coating layer which covers the surface of the silica gel particle carrier carrying the silver thiosulfate complex salt, any of organic silicon compound, wax or stearic acid compound may be used. A preferred material for the coating material layer is however silicon dioxide obtained by hydrolyzing an organic silicon compound. As a method for forming the silicon dioxide coating layer, there is exemplified a solgel method of hydrolyzing an alcoholic solution of an alkoxysilane by adding water to the solution. A preferred alkoxysilane has an alkoxyl group having from 1 to 4 carbon atoms. A preferred alcohol has an alkyl group having from 1 to 4 carbon atoms. The suitable amount of the coating layer is 100–200 parts by weight for 100 parts by weight of the silica gel particles carrying the silver thiosulfate complex salt.

By forming the coating material layer, the above-mentioned antibacterial composition is made to have a preferred slow releasing property. Therefore, it has a very scarce detrimental effect for polluting the environment. In addition, by the provision of the coating material layer, a heat stability of the silver thiosulfate complex salt carried on the carrier is improved.

The antibacterial composition of the present invention, prepared by causing the silica gel having an equilibrium water content of 10% by weight or smaller at room temperature and ordinary humidity (25° C., relative humidity: 70%) to carry a potassium salt of the silver thiosulfate complex, is the most excellent in its heat-resistant property, and can withstand a heating at 250° C. for 20 minutes or shorter. Further, one obtained by causing an ordinary silica gel to carry a potassium salt of the silver thiosulfate complex can withstand a heating at 250° C. for 1 minute or shorter. On the other hand, one obtained by causing the silica gel having an equilibrium water content of 10% or smaller at room temperature and ordinary humidity (25° C., relative humidity: 70%) to carry a sodium salt of the silver thiosulfate complex is inferior in its heat-resistant property to the above-mentioned ones, and can only withstand a heating at 210° C. for 5 minutes or shorter. However, one obtained by causing an ordinary silica gel having a larger equilibrium water content to carry a sodium salt of the silver thiosulfate complex is further inferior to the above-mentioned ones and can only withstand a heating at 210° C. for 1 minute or shorter, and thus is not practical.

As described in the above, according to the present invention, it is possible to obtain the antibacterial composition which demonstrates a stable antibacterial activity on the surface of the resin product, has a heat-resistant property sufficient for avoiding its decomposition or discoloration at the resin molding temperature, and hardly becomes a cause for an environmental pollution.

EXAMPLE 1

Silver acetate ($CH_3COOAg$) was dissolved in pure water at 60° C. or lower in a proportion of 7.7 g/liter. To this solution, potassium sulfite ($K_2SO_3$) in a proportion of 2.7 g for 1 g of $CH_3COOAg$ was added and then stirred to dissolve therein. Thereafter, potassium thiosulfate ($K_2S_2O_3$) was added to the mixture in a proportion of 6.6 g for 1 g of $CH_3COOAg$ and stirred to dissolve. In this manner, an aqueous solution of silver thiosulfate complex salt was prepared.

As a carrier for carrying the thus obtained aqueous solution, this Example employed the silica gel available from SHIONOGI & CO. LTD., Japan, under a trade designation: Carplex CS-5 (equilibrium water content: 3.6% at relative humidity: 90%, number of —OH groups on the surface: $1.5/nm^2$, weight loss by drying: 1.1%, and mean particle size: 2.3 μm).

By dispersing the silica gel particles in the above-mentioned aqueous solution of silver thiosulfate complex salt under the condition of room temperature and atmospheric pressure, the solution was adsorbed in the silica gel particles. After sufficiently impregnating the silica gel with the aqueous solution of silver thiosulfate complex salt so that the entire amount of the solution can be adsorbed in the silica gel particles, the impregnated silica gel particles were dried. That is, in preparing the silica gel particles carrying the silver complex salt, a so-called "spray drying method" is employed, whereby a slurry, obtained by adding the silica gel to the above-mentioned solution, was dripped on a rotating disk, and the dripped slurry was atomized and was then dried in a heated air at about 160° C. The amount of the silver complex salt to be carried was 3% by weight of the carrier when converted into the amount of silver.

Next, 1 g of the above-mentioned silica gel carrying the silver complex salt was dispersed in a solution prepared by dissolving 1 ml of tetraethoxysilane in 1 ml of ethanol. After the dispersion was intimately mixed, the tetraethoxysilane in the obtained dispersion was hydrolyzed by dripping about 0.2 ml of pure water to form silicon dioxide. The silicon dioxide layer thus formed as the hydrolyzed product of the tetraethoxysilane is caused to coat at least part of the surface of the above-mentioned silica gel. Then, the coated silica gel is dried.

EXAMPLE 2

In preparing an antibacterial composition, procedures similar to those in Example 1 were generally followed except for the use of a silica gel having an equilibrium water content of 25% by weight at 25° C. and a relative humidity of 70%, in lieu of the silica gel used in Example 1.

Comparative Example 1

In preparing another composition, the same carrier as that of Example 1 was used and similar procedures to those in Example 1 were followed except for an omission of the silver acetate from the raw material used in preparing the aqueous solution of Example 1.

Comparative Example 2

In preparing another composition, procedures similar to those in Example 1 were generally followed except for the use of an aqueous solution of silver acetate, in lieu of the aqueous solution of silver thiosulfate complex salt.
Evaluation The results of differential thermal analyses performed on the compositions of Example 1, Example 2 and the same silica gel as that used in Example 2 will be described below.

First, about 10 mg of alumina, which will not be thermally changed in the region of the measuring temperature, was placed on an aluminum pan. Each of the composition powders to be measured was weighted and placed on a separate aluminum pan. The amounts of the compositions used in these differential thermal analyses were 15.064 mg for the composition of Example 1, 15.097 mg for that of Example 2, and 8.538 mg for that of the silica gel, respectively. These pans were placed under an atmosphere which raised its temperature at a rate of 10° C./min., and the temperature differences among the individual pans were measured. The results of the measurements is shown as the differential thermal analysis curves in FIG. 8.

Figure 3:
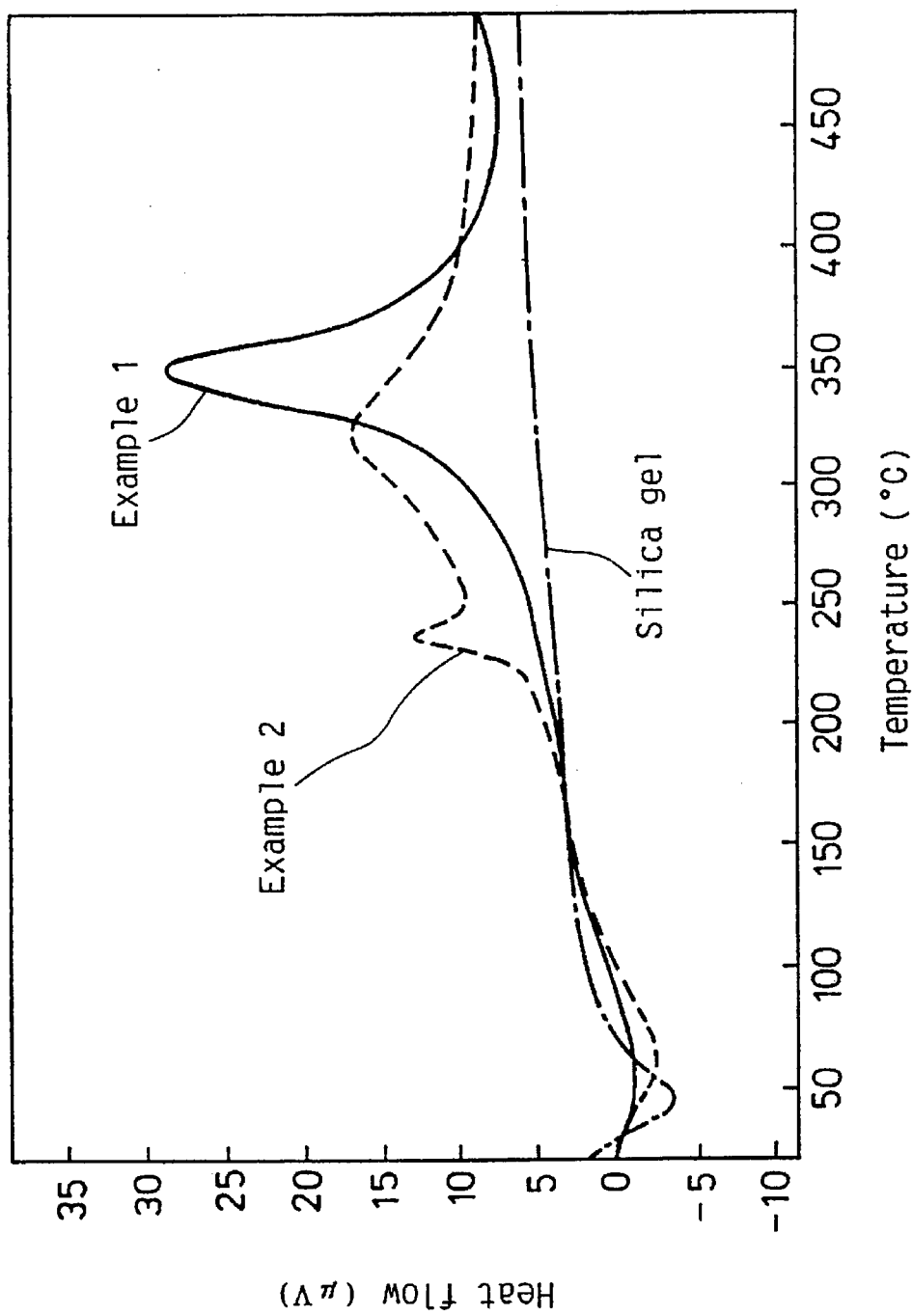
FIG. 3 is a diagram showing thermal differential analysis curves obtained with the antibacterial compositions of the present invention and the silica gel.

As clearly shown by FIG. 3, the composition of Example 2 has a peak in its differential thermal analysis curve at a vicinity of 230° C. and it is appreciated that the silver complex salt contained therein is thermally decomposed. In contrast, the composition of Example 1 has no remarkable peak in its differential thermal analysis curve at a temperature range between 200° C. and 270° C., and it is appreciated that the silver complex salt contained therein is stable in this temperature range.

Next, after dispersing each 1 g of the compositions of Example 1, Example 2, and Comparative Example 2 in 100 ml of pure water, the obtained dispersions were filtered through a No.5 filter paper of 12 cm to prepare individual filtrates. When 0.1 g of sodium chloride was added to the individual filtrates, white turbidity was produced only in the filtrate of Comparative Example 2.

Test pieces of the resin molded products, each having a size of 5 cm×7 cm and a thickness of 2 mm, were prepared by mixing each 1.0 part by weight of the compositions of Example 1, Example 2, and Comparative Example 1, with 100 parts by weight of polypropylene resin, then mechanically stirred, and thereafter molded by an injection molding machine having a nozzle temperature of 220° C. Antifungal and antibacterial tests were performed on the thus obtained resin molded products in the following manner.

Antifungal Tests

The tests were performed in accordance with the procedure of halo test by mildew proof examination for textile taken from the test for resistance to fungus defined in Japanese Industrial Standard (JIS Z 2911). Fungi used in the tests were *Cladosporium cladosporioides, Chaetomium globosum, Penicillium citrinum* and *Asperigillus niger*, respectively. One (1) ml of a suspension (added with agar) including spores of each of the fungi was titrated on the test piece, and after the test piece carrying the titrated suspension was incubated under an atmosphere saturated with steam at 25° C. for 14 days, the growth of each of the fungi was visually inspected. In evaluation, it was regarded to be "effective" if no growth of fungus is recognized outside of the titrated agar placed on the test pieces.

Antibacterial Tests

Bacteria used in the test were *Escherichia coli, Staphylococcus aureus* and *Bacillus subtillis*, and the tests were performed in a method analogous to the known dripping method. Evaluation of the antibacterial activity was performed 24 hours after the inoculation of bacteria. It was regarded to be "effective" if the number of bacteria after 24 hours was below $10^2$ CFU for the initial number of bacteria of $10^4$ CFU or above.

Results of the tests are summarized in Table 1 below.

TABLE 1

|  | Mixture of 4 kinds of fungi | E.coli | S.aureus | B.subtillis |
| --- | --- | --- | --- | --- |
| Example 1 | Effective | Effective | Effective | Effective |
| Example 2 | Effective | Effective | Effective | Effective |
| Comparative Example 1 | Not Effective | Not Effective | Not Effective | Not Effective |

From the result summarized in Table 1, it is appreciated that each of the antibacterial compositions of Example 1 and 2 has a practical antifungal and antibacterial performance.

Further, an antibacterial composition was also obtained by substituting the potassium salt with a sodium salt in the preparation of the above-mentioned complex salt solution. Although the characteristics of the thus obtained composition were somewhat inferior to those prepared by using potassium salt, the composition itself was practically usable without any inconvenience.

EXAMPLE 3

Silica gel of B-type defined by JIS and having a mean particle size of 3 μm was subjected to a heat treatment in an electric furnace placed in the atmosphere at various temperatures listed in Table 2 below for 2 hours. Each of the heat-treated silica gels was pulverized in a dried state and sieved to have a particle size of 10 μm or smaller.

Each of the heat-treated and pulverized silica gel was caused to carry the potassium salt of the silver thiosulfate complex at 3% by weight in a percent value converted into the amount of silver, and the surfaces of the silica gel particles were coated with silicon dioxide, in a manner similar to those in Example 1.

In order to measure the discolorations of the antibacterial compositions comprising the above-mentioned silica gels treated at the various temperatures listed in below-mentioned Table 2 and carrying the silver complex salts, resin molded product samples were prepared by mixing 1.0 part by weight of the various antibacterial compositions with 100 parts by weight of polypropylene resin and molding the mixture at a nozzle temperature of 250° C. Results of the measurement are shown in the Table 2. The Table 2 indicates the relationships between the heat-treatment temperatures of the silica gel carriers and the numbers of —OH groups on the surface of the silica gel carriers, and the changes in color by visual inspection.

TABLE 2

| Heating temperature (°C.) | Change in color | Number of —OH groups on the surface (group/nm$^2$) |
| --- | --- | --- |
| No heating | Colored in brown | 10 |
| 100 | Colored in brown | 9 |
| 500 | Colored in brown | 3 |
| 600 | Slightly colored in brown | 2 |
| 700 | Very slightly colored in brown | 1.8 |
| 800 | Transparent and not colored | 1.5 |
| 1000 | Transparent and not colored | 1 |
| 1200 | Transparent and not colored | 1 |
| 1400 | White spots by sintering | <1 |

Condition of the Heat Treatment

As shown in the above Table 2, the silica gels subjected to the heat treatment under 800° C. were colored in brown when they were incorporated in the resin together with the antibacterial composition by kneading and molded into the resin molded products at 250° C. The silica gels being subjected to the heat treatment between 800° C. and 1200° C. were transparent and not colored when they were incorporated in the resin together with the antibacterial composition by kneading and molded into the resin molded products at 250° C. Further, when the heat-treatment temperature of the silica gel was high above 1400° C., the silica gel was sintered to become silica crystal that produces white spots when it was mixed to and kneaded in the resin.

EXAMPLE 4

Antibacterial compositions were prepared in a manner similar to those in Example 1, except for varying the proportion of potassium thiosulfate ($K_2S_2O_3$) added at the silver complex salt preparing step, so that the molar ratio of $S_2O_3^{2-}/Ag^+$ would be a number listed in Table 3 below. Each 1.5 parts by weight of these antibacterial compositions was mixed with 100 parts by weight of polypropylene resin and molded at 220° C. or 240° C. Table 3 indicates the relationships between the varying molar ratio of $S_2O_3^{2-}/Ag^+$ and the presence or absence of the discoloration, as well as the presence or absence of the antibacterial activity of the molded products which depend on the temperature during the molding process.

TABLE 3

| Molar ratio of $S_2O_3^{2-}/Ag+$ | Discoloration of the molded product on the molding temperature | | Antibacterial property of the molded product on the molding temperature | |
|---|---|---|---|---|
| | 220° C. | 240° C. | 220° C. | 240° C. |
| 0.7 | Brown | Brown | ± | ± |
| 1 | No | No | + | + |
| 2 | No | No | + | + |
| 3 | No | No | + | + |
| 4 | Brown | Brown | ± | − |
| 5 | No | No | + | + |
| 6 | No | No | + | + |
| 7 | No | No | + | + |
| 8 | No | No | + | + |
| 9 | *1 | *1 | *1 | *1 |

Brown: colored in brown, No: no color change
+: presence of antibacterial property
±: presence of weak antibacterial property
−: absence of antibacterial property
*1: Gave no molded product Stability of the Composition As shown in Table 3 above, it was found that compositions having a molar ratio of $S_2O_3^{2-}/Ag^+$ under 1 were unstable, whereas those having a molar ratio in excess of 8 demonstrated a precipitation of potassium thiosulfate ($K_2S_2O_3$) in a large quantity and thus had a poor workability. Further, the composition of the molar ratio of 4 had a poor heat-resistant property, and, in particular, a discoloration of the antibacterial composition was observed when the molding temperature approached to 240° C. From these results, it is concluded that a preferable heat-resistant property of the composition can be obtained with a molar ratio of $S_2O_3^{2-}/Ag^+$ in a range between 1 and 3 or a range between 5 and 8. In case of employing sodium thiosulfate ($Na_2S_2O_3$) in lieu of the potassium salt, although no discoloration was observed and the antibacterial activity was kept at the molding temperature at 220° C., the composition was made inferior to that of the potassium salt at the molding temperature of 240° C.

EXAMPLE 5

Another antibacterial composition was prepared in a manner similar to those in Example 1 except that potassium hydrogen sulfite was used in lieu of potassium sulfite with the same concentration of sulfite ions and the silica gel carrying the silver thiosulfate complex salt was not coated with silicon dioxide.

A resin molded product was obtained by mixing 5 parts by weight of this antibacterial composition with 100 parts by weight of unsaturated polyester resin, and the mixture was then molded into the product at a nozzle temperatures of 220° C. and 240° C. within one minute. No discoloration was observed with the molded product.

Although the present invention has been described in terms of the presently preferred embodiments, it is to be understood that such disclosures are not to be interpreted as limiting. Various alterations and modification will no doubt become apparent to those skilled in the art to which the present invention pertains, after having read the above disclosure. Accordingly, it is intended that the appended claims be interpreted as covering all alterations and modifications as fall within the true spirit and scope of the invention.

What is claimed is:

1. An antibacterial composition comprising a potassium salt of silver thiosulfate complex carried on silica gel particles that have been subjected to a heat treatment at a temperature of from 800° C. to 1200° C. and that have an equilibrium water content of 10 wt % or less at 25° C. and 70% relative humidity and that have hydroxyl (—OH) groups on their surfaces in 2 groups/nm$^2$ or less, wherein said potassium salt has a molar ratio of $S_2O_3^{2-}/Ag^+$ in a range between 1 and 3 or in a range between 5 and 8, and wherein said silica gel carrying said potassium salt is characterized by diffraction lines of $K_2SO_4$ and $K_2S_2O_6$ and by some intensity of diffraction at 8.7°, 9.4°, 9.8° and 11.2° in a diffraction angle 2θ in a diffraction angle 2θ in an X-ray diffraction pattern by means of Kα line of Cu and wherein a coating material covers at least some of the silver thiosulfate complex salt that is carried on said silica gel particles, said coating material being selected from the group consisting of organic silicon compound, wax, stearic acid and silicon dioxide and providing for a controlled release of the silver thiosulfate complex salt.

2. The antibacterial composition in accordance with claim 1, wherein said coating material is silicon dioxide formed by means of hydrolysis of an alkoxysilane.

3. An antibacterial composition comprising a sodium salt of silver thiosulfate complex carried on silica gel particles that have been subjected to a heat treatment at a temperature of from 800° C. to 1200° C. and that have an equilibrium water content of 10 wt % or less at 25° C. and 70% relative humidity and that have hydroxyl (—OH) groups on their surfaces in 2 groups/nm$^2$ or less, wherein said sodium salt has a molar ratio of $S_2O_3^{2-}/Ag^+$ in a range between 1 and 3 or in a range between 5 and 8, and wherein said silica gel carrying said sodium salt is characterized by diffraction lines of $Na_2SO_4$ and $Ag_2O$ and by some intensity of diffraction at 10.3°, 11.2°, 11.9° and 12.3° in a diffraction angle 2θ in an X-ray diffraction pattern by means of Kα line of Cu and wherein a coating material covers at least some of the silver thiosulfate complex salt that is carried on said silica gel particles, said coating material being selected from the group consisting of organic silicon compound wax, stearic acid and silicon dioxide and providing for a controlled release of the silver thiosulfate complex salt.

4. The antibacterial composition in accordance with claim 3, wherein said coating material is silicon dioxide formed by means of hydrolysis of an alkoxysilane.

* * * * *